United States Patent [19]

Schroeck

[11] Patent Number: 4,507,215
[45] Date of Patent: Mar. 26, 1985

[54] PHOSPHORUS-CONTAINING METAL SALT/OLEFIN COMPOSITIONS AND REACTION PRODUCTS OF SAME WITH ACTIVE SULFUR

[76] Inventor: Calvin W. Schroeck, 873 E. 331st St., Eastlake, Ohio 44094

[21] Appl. No.: 488,569

[22] Filed: Apr. 25, 1983

[51] Int. Cl.³ .............................................. C10M 1/48
[52] U.S. Cl. .............................. 252/32.7 E; 252/46.7; 252/35
[58] Field of Search ................. 252/32.7 E, 35, 46.7; 260/429 R

[56] References Cited

U.S. PATENT DOCUMENTS

| | | | |
|---|---|---|---|
| 2,794,780 | 6/1957 | Wystrach et al. | 252/32.7 |
| 2,809,979 | 10/1957 | Craig | 260/429.9 |
| 3,211,648 | 10/1965 | Hopkins et al. | 252/32.7 |
| 3,267,033 | 8/1966 | Allen | 252/32.7 |
| 3,335,158 | 8/1967 | Goldsmith | 260/429.9 |
| 3,390,082 | 6/1968 | Le Suer et al. | 252/32.7 |
| 3,405,064 | 10/1968 | Miller | 252/51.5 |
| 4,010,106 | 3/1977 | Rothert | 252/32.7 E |
| 4,032,461 | 6/1977 | Hoke | 252/46.7 |
| 4,175,043 | 11/1979 | Howdysky | 252/32.7 E |
| 4,191,659 | 3/1980 | Davis | 252/45 |
| 4,263,150 | 4/1981 | Clason et al. | 252/32.7 |
| 4,288,335 | 9/1981 | Rivier | 252/32.7 |
| 4,289,635 | 9/1981 | Schroeck | 252/32.7 |
| 4,293,430 | 10/1981 | Rivier | 252/32.7 |
| 4,308,154 | 12/1981 | Clason et al. | 252/32.7 E |
| 4,322,478 | 3/1982 | Forsberg | 428/471 |
| 4,326,972 | 4/1982 | Chamberlin | 252/33.3 |
| 4,417,990 | 11/1983 | Clason et al. | 252/32.7 E |
| 4,456,538 | 6/1984 | Ripple | 252/32.7 E |

FOREIGN PATENT DOCUMENTS 1105729 5/1966 United Kingdom .

Primary Examiner—Jacqueline V. Howard

[57] ABSTRACT

A composition comprising: (A) a metal salt of (A)(I) at least one acid of the formula

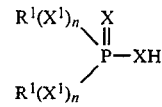

wherein each X and $X^1$ is independently oxygen or sulfur, each n is zero or one, and each $R^1$ is independently the same or different hydrocarbon based group, and (A)(II) at least one carboxylic acid of about 2 to about 40 carbon atoms, the ratio of equivalents of (A)(I) to equivalents of (A)(II) being in the range of about 0.5:1 to about 1:0; and (B) an olefinically unsaturated compound capable of reacting with active sulfur. Compositions comprising the foregoing composition reacted with active sulfur are also disclosed. Lubricants and functional fluids comprising the foregoing compositions are disclosed. A process comprising reacting active sulfur with an olefinically unsaturated compound in the presence of component (A) is also disclosed.

46 Claims, No Drawings

PHOSPHORUS-CONTAINING METAL SALT/OLEFIN COMPOSITIONS AND REACTION PRODUCTS OF SAME WITH ACTIVE SULFUR

TECHNICAL FIELD

This invention relates to phosphorus-containing metal salt/olefin compositions and to the reaction products of such compositions with active sulfur. More particularly, this invention relates to compositions comprising: metal salts of phosphorus-containing acids or metal salts of mixtures of such phosphorus-containing acids and carboxylic acids, and olefinically unsaturated compounds capable of reacting with active sulfur; and the reaction products of such compositions with active sulfur. This invention also relates to compositions comprising metal salts of phosphorus-containing acids and to metal salts of mixtures of such phosphorus-containing acids and carboxylic acids that are relatively free of active sulfur. This invention relates to a process for reacting an olefin with active sulfur in the presence of a metal salt of a phosphorus-containing acid or a metal salt of mixtures of such phosphorus-containing acid and a carboxylic acid. This invention also relates to lubricants and functional fluids comprising the foregoing compositions.

BACKGROUND OF THE INVENTION

Metal salts of phosphorodithioic acids are known lubricant additives. See, for example, U.S. Pat. Nos. 3,390,082 and 4,326,972. Metal salts of mixtures of phosphorodithioic acids and carboxylic acids are also known lubricant additives. See, for example, U.S. Pat. No. 4,308,154.

Preparations of phosphorodithioic acid usually involve the reaction of phosphorus pentasulfide ($P_2S_5$) and an alcohol or a phenol. A problem that arises with these preparations is that they often result in levels of active sulfur that are unacceptable for certain applications due to the corrosive nature of active sulfur. For example, certain hydraulic fluids containing an excess of about 300 ppm active sulfur (as measured by IP-155) may under various circumstances stain or corrode copper and similar materials.

The sulfurization of olefinically unsaturated compounds at relatively low temperatures of about 140° C., for example, requires relatively long reaction times and the products of such sulfurizations tend to have levels of active sulfur that are unacceptable for various applications such as lubricants or functional fluids intended for use with copper or similar metals. When the sulfurization is conducted at higher temperatures of about 150°–180° C., for example, very dark to black products are often obtained which when employed in lubricants or functional fluids usually result in dark oil solutions that are commercially unacceptable.

It would be advantageous to provide metal salts of phosphorus-containing acids, or metal salts of mixtures of such phosphorus-containing acids and carboxylic acids that have sufficiently low levels of active sulfur so that such salts or lubricants or functional fluids containing such salts would not stain or corrode copper or similar materials. It would also be advantageous to sulfurize olefinically unsaturated compounds at relatively low reaction temperatures (i.e., below about 140° C.) and relatively short reaction times, and provide compositions that are relatively light in color and have sufficiently low levels of active sulfur so that such compositions or lubricants or functional fluids containing such compositions would not stain or corrode copper or similar materials.

U.S. Pat. No. 4,289,635 discloses molybdenum-containing compositions prepared by reacting an olefinically unsaturated compound capable of reacting with active sulfur with a composition prepared by reacting (a) a phosphorus containing acid represented by the formula

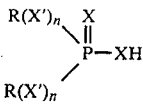

wherein each X and X' is independently oxygen or sulfur, each n is 0 or 1 and each R is independently the same or different hydrocarbon-based radical, and (b) at least one hexavalent molybdenum oxide compound, and (c) hydrogen sulfide, in the presence of (d) a polar solvent. These compositions are described as being useful as additives for lubricants.

SUMMARY OF THE INVENTION

The present invention provides for metal salts of phosphorus-containing acids, and metal salts of mixtures of such phosphorus-containing acids and carboxylic acids, that have sufficiently low levels of active sulfur so that such salts as well as lubricants or functional fluids containing such salts are non-staining and non-corrosive to copper and similar materials. The invention further provides for enhanced sulfurizations of olefinically unsaturated compounds at relatively low reaction temperatures and relatively short reaction times to provide compositions that are relatively light in color and have sufficiently low levels of active sulfur so that such compositions as well as lubricants or functional fluids containing such compositions are non-staining and non-corrosive to copper and similar materials.

The present invention contemplates the provision of a composition comprising (A) a metal salt of (A)(I) at least one acid of the formula

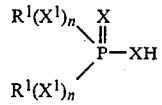

wherein each X and $X^1$ is independently oxygen or sulfur, each n is zero or one, and each $R^1$ is independently the same or different hydrocarbon based group, and (A)(II) at least one carboxylic acid of about 2 to about 40 carbon atoms, the ratio of equivalents of (A)(I) to equivalents of (A)(II) being in the range of about 0.5:1 to about 1:0; and (B) an olefinically unsaturated compound, capable of reacting with active sulfur, the ratio of equivalents of component (A) to equivalents of component (B) being in the range of about 1000:1 to about 1:5.

Further, the present invention provides for a composition comprising the reaction product of (A) a metal salt of (A)(I) at least one acid of the formula

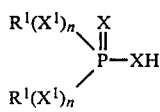

wherein each X and X¹ is independently oxygen or sulfur, each n is zero or one, and each R¹ is independently the same or different hydrocarbon based group, and (A)(II) at least one carboxylic acid of about 2 to about 40 carbon atoms, the ratio of equivalents of (A)(I) to equivalents of (A)(II) being in the range of about 0.5:1 to about 1:0; (B) an olefinically unsaturated compound; and (C) active sulfur, component (A) being present in an effective amount to promote the reaction between components (B) and (C) and/or between components (A), (B) and (C) sufficiently to consume substantially all of component (C) at a reaction temperature below about 140° C.

The invention further provides for additive concentrates, lubricant compositions and functional fluids comprising the foregoing compositions.

The invention further provides for a process comprising reacting active sulfur with an olefinically unsaturated compound at a temperature below about 140° C., in the presence of (A) a metal salt of (A)(I) at least one acid of the formula

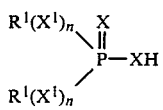

wherein each X and X¹ is independently oxygen or sulfur, each n is zero or one, and each R¹ is independently the same or different hydrocarbon based group, and (A)(II) at least one carboxylic acid of about 2 to about 40 carbon atoms, the ratio of equivalents of (A)(I) to equivalents of (A)(II) being in the range of about 0.5:1 to about 1:0, component (A) being present in an effective amount to promote the consumption of substantially all of said active sulfur. The reaction products of this process, as well as concentrates, lubricants and functional fluids comprising such reaction products are within the scope of the present invention.

DETAILED DESCRIPTION OF THE PREFERRED EMBODIMENT

The term "hydrocarbon-based group" is used throughout this specification and in the appended claims to denote a group having a carbon atom directly attached to the remainder of the molecule and having predominantly hydrocarbon character within the context of this invention. Such groups include the following:

(1) Hydrocarbon groups; that is, aliphatic, (e.g., alkyl or alkenyl), alicyclic (e.g., cycloalkyl or cycloalkenyl), aromatic, aliphatic- and alicyclic-substituted aromatic, aromatic-substituted aliphatic and alicyclic groups, and the like, as well as cyclic groups wherein the ring is completed through another portion of the molecule (that is, the two indicated substituents may together form a cyclic group). Such groups are known to those skilled in the art; examples include methyl, ethyl, butyl, hexyl, octyl, decyl, dodecyl, tetradecyl octadecyl, eicosyl, cyclohexyl, phenyl and naphthyl (all isomers being included).

(2) Substituted hydrocarbon groups; that is, groups containing non-hydrocarbon substituents which, in the context of this invention, do not alter predominantly hydrocarbon character of the group. Those skilled in the art will be aware of suitable substituents (e.g., halo, hydroxy, alkoxy, carbalkoxy, nitro, alkylsulfoxy).

(3) Hetero groups; that is, groups which, while predominantly hydrocarbon in character within the context of this invention, contain atoms other than carbon present in a chain or ring otherwise composed of carbon atoms. Suitable hetero atoms will be apparent to those skilled in the art and include, for example, nitrogen, oxygen and sulfur.

In general, no more than about three substituents or hetero atoms, and preferably no more than one, will be present for each 10 carbon atoms in the hydrocarbon-based group.

Component (A)

Component (A)(I), the phosphorus-containing acids of the present invention, can be represented by the general formula

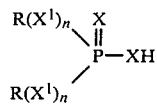

wherein each X and X¹ is independently oxygen or sulfur, each n is zero or one, and each R¹ is independently the same or different hydrocarbon based group. Illustrative examples of some preferred phosphorus-containing acids are:

1. Dihydrocarbyl phosphinodithioic acids corresponding to the formula,

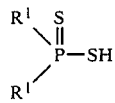

2. S-hydrocarbyl hydrocarbyl phosphonotrithioic acids corresponding to the formula,

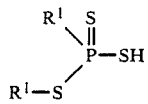

3. O-hydrocarbyl hydrocarbyl phosphonodithioic acids corresponding to the formula,

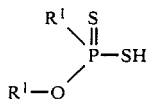

4. S,S-dihydrocarbyl phosphorotetrathioic acids corresponding to the formula,

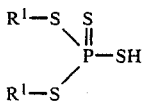

5. O,S-dihydrocarbyl phosphorotrithioic acids corresponding to the formula,

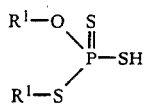

6. O,O-dihydrocarbyl phosphorodithioic acids corresponding to the formula,

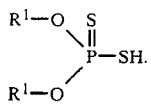

Preferred acids of the formula

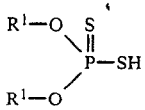

are readily obtainable by the reaction of phosphorus pentasulfide ($P_2S_5$) and an alcohol or a phenol. The reaction involves mixing at a temperature of about 20° to about 200° C., four moles of alcohol or a phenol with one mole of phosphorus pentasulfide. Hydrogen sulfide is liberated in this reaction. The oxygen-containing analogs of these acids are conveniently prepared by treating the dithioic acid with water or steam which, in effect, replaces one or both of the sulfur atoms.

The preferred phosphorus-containing acids are phosphorus- and sulfur-containing acids. These preferred acids preferably include those acids wherein at least one X is sulfur, and more preferably both X are sulfur, at least one $X^1$ is oxygen or sulfur, more preferably both $X^1$ are oxygen and n is 1. Mixtures of these acids may be employed in accordance with this invention.

Each $R^1$ is independently a hydrocarbon-based group that is preferably free from acetylenic and usually also from ethylenic unsaturation and have from about 1 to about 50 carbon atoms, preferably from about 1 to about 30 carbon atoms, and more preferably from about 3 to about 18 carbon atoms. In a particularly advantageous embodiment each $R^1$ is the same or different and has from about 4 to about 8 carbon atoms. Each $R^1$ can be, for example, isopropyl, isobutyl, 4-methyl-2-pentyl, 2-ethylhexyl, iso-octyl, etc. Each $R^1$ is most often identical to each other, although they may be different and either or both may be mixtures. Each $R^1$ is preferably alkyl, and most desirably branched alkyl.

Component (A)(II) may be a monocarboxylic or polycarboxylic (e.g., di-, tri-, etc.) acid, usually containing from 1 to about 3 carboxy groups and preferably only 1. It may contain from about 2 to about 40, preferably from about 2 to about 20 carbon atoms, and advantageously about 5 to about 20 carbon atoms. The preferred carboxylic acids are those having the formula $R^3COOH$, wherein $R^3$ is an aliphatic or alicyclic hydrocarbon-based group of about 1 to about 40 carbon atoms, preferably about 1 to about 20 carbon atoms, that is preferably free from acetylenic unsaturation. Suitable acids include acetic, propionic, butanoic, pentanoic, hexanoic, octanoic, nonanoic, decanoic, dodecanoic, tetradecanoic, hexadecanoic, octadecanoic and eicosanoic acids, as well as olefinic acids such as acrylic, oleic, linoleic, and linolenic acids and linoleic acid dimer. For the most part, $R^3$ is methyl or a saturated aliphatic group and especially a branched alkyl group such as the isopropyl or 3-heptyl group. Illustrative polycarboxylic acids are oxalic, malonic, succinic, alkyl- and alkenyl-succinic, glutaric, adipic, pimelic, sebacic, maleic, fumaric and citric acids.

Component (A) is a metal salt of component (A)(I) or a metal salt of a mixture of components (A)(I) and (A)(II). The metals for component (A) are the Group I metals, the Group II metals, aluminum, tin, cobalt, lead, zinc, manganese and nickel as well as mixtures of two or more of these metals. The preferred salts are those of zinc. When component (A) is a metal salt of component (A)(I) it can be prepared by reacting component (A)(I) with a suitable metal base. When component (A) is a metal salt of a mixture of components (A)(I) and (A)(II) it can be prepared by merely blending a metal salt of component (A)(I) with a metal salt of component (A)(II) in the desired ratio.

The ratio of equivalents of component (A)(I) to equivalents of component (A)(II) is in the range of about 0.5:1 to about 1:0. The specification of a ratio of equivalents of (A)(I) to equivalents of (A)(II) of 1:0 is a shorthand method used herein and in the appended claims of identifying component (A) as a metal salt of component (A)(I) only. The ratio of equivalents of (A)(I) to equivalents of (A)(II) can be about 0.5:1 to about 500:1, preferably 0.5:1 to about 200:1, and more preferably about 0.5:1 to about 100:1. When component (A)(II) is a low molecular weight acid (i.e. about three carbon atoms or less) such as acetic acid or proprionic acid, a particularly advantageous ratio of equivalents of (A)(I) to equivalents of (A)(II) is about 400:1 to about 50:1, preferably about 100:1 to about 200:1. When component (A)(II) has more than about three carbon atoms, a particularly advantageous ratio is in the range of 0.5:1 to about 50:1, preferably about 0.5:1 to about 20:1.

The equivalent weight of component (A)(I) can be determined by dividing the molecular weight of component (A)(I) by the number of —PXXH groups. These can usually be determined from the structural formula of component (A)(I) or empirically through well known titration procedures. The number of equivalents of component (A)(I) can be determined by dividing the weight of component (A)(I) by its equivalent weight.

The equivalent weight of component (A)(II) can be determined by dividing the molecular weight of component (A)(II) by the number of —COOH groups present. These can usually be determined from the structural formula of component (A)(II) or empirically through well known titration procedures. For example, a succinic acid has an equivalent weight of one-half its molecular weight. The number of equivalents of component (A)(II) can be determined by dividing the weight of component (A)(II) by its equivalent weight.

The total number of equivalents of component (A) can be determined by adding the number of equivalents of component (A)(I) and the number of equivalents of component (A)(II).

A second and preferred method for preparing the metal salts of mixtures of components (A)(I) and (A)(II) is to prepare a mixture of the acids (components (A)(I) and (A)(II)) in the desired ratio and to react the acid mixture with a suitable metal base. When this method of preparation is used, it is frequently possible to prepare a neutral salt or a salt having more or less than the metal present in the corresponding neutral salt.

The term "neutral salt" refers to salts characterized by metal content equal to that which would be present according to the stoichiometry of the metal and the particular organic compound reacted with the metal, i.e., component (A)(I) or mixtures of components (A)(I) and (A)(II). Thus, if a phosphorodithioic acid,

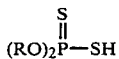

is neutralized with a basic metal compound, e.g., zinc oxide, the neutral metal salt produced would contain one equivalent of zinc for each equivalent of acid, i.e.,

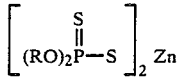

However, with the present invention, component (A) can contain more or less than the stoichiometric amount of metal. The products containing less than the stoichiometric amount of metal are acidic materials. The products containing more than the stoichiometric amount of metal are overbased materials. For example, salts of component (A) containing 80% of the metal present in the corresponding neutral salt are acidic, while salts of component (A) containing 110% of the metal present in the corresponding neutral salt are overbased.

Component (A) has about 80% to about 200%, preferably about 100% to about 150%, more preferably about 100% to about 135%, and advantageously about 103% to about 110% of the metal present in the corresponding neutral salt.

Variants of the above-described methods may also be used to prepare the mixed metal salts of this invention. For example, a metal salt of component (A)(I) or (A)(II) may be blended with the free acid as component (A)(II) or (A)(I), respectively, and the resulting blend reacted with additional metal base.

Suitable metal bases for the preparations of component (A) include the free metals previously enumerated and their oxides, hydroxides, alkoxides and basic salts. Examples are sodium hydroxide, sodium methoxide, sodium carbonate, potassium hydroxide, potassium carbonate, magnesium oxide, magnesium hydroxide, calcium hydroxide, calcium acetate, zinc oxide, zinc acetate, lead oxide, nickel oxide and the like.

The temperature at which the metal salts of component (A) are prepared is generally between about 30° and about 150° C., preferably up to about 125° C. If component (A) is prepared by neutralization of a mixture of acids with a metal base, it is preferred to employ temperatures above about 50° and especially above about 75°. It is frequently advantageous to conduct the reaction in the presence of a substantially inert, normally liquid organic diluent such as naphtha, benzene, xylene, mineral oil or the like. If the diluent is mineral oil or is physically and chemically similar to mineral oil, it frequently need not be removed before using the component (A) in the compositions of the present invention.

Component (B)

The olefinically unsaturated compounds of the present invention are those compounds that are capable of reacting with active sulfur. These compounds are diverse in nature. They contain at least one olefinic double bond, which is defined as a non-aromatic double bond; that is, one connecting two aliphatic carbon atoms. It its broadest sense, the olefin may be defined by the formula $R^4R^5C=CR^6R^7$, wherein each of $R^4$, $R^5$, $R^6$ and $R^7$ is hydrogen or an organic group. In general, the R groups in the above formula which are not hydrogen may be satisfied by such groups as $-C(R^8)_3$, $-COOR^8$, $-CON(R^8)_2$, $-COON(R^8)_4$, $-COOM$, $-CN$, $-R^8COOR^8$, $-R^8CON(R^8)_2$, $-R^8COON(R^8)_4$, $-R^8COOM$, $-R^8CN$,

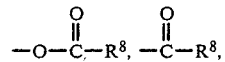

$-R^8$, $-X$, $-R^8X$, $-YR^8$, $-R^8YR^8$, $-R^8N(R^8)_2$, or $-Ar$, wherein:

Each $R^8$ is independently hydrogen, alkyl, alkenyl, aryl, substituted alkyl, alkylene, substituted alkylene, substituted alkenyl or substituted aryl, with the proviso that any two $R^8$ groups can be alkylene or substituted alkylene whereby a ring of up to about 12 atoms is formed;

M is one equivalent of a metal cation (preferably Group I or II, e.g., sodium, potassium, barium, calcium);

X is halogen (e.g., chloro, bromo, or iodo);

Y is oxygen or divalent sulfur;

Ar is an aryl or substituted aryl radical of up to about 12 carbon atoms in the substituent.

Any two of $R^4$, $R^5$, $R^6$ and $R^7$ may also together form an alkylene or substituted alkylene group; i.e., the olefinic compound may be alicyclic.

The natures of the substituents in the substituted moieties described above are not normally a critical aspect of the invention and any such substituent is useful so long as it is or can be made compatible with lubricating environments and does not interfere under the contemplated reaction conditions. Thus, substituted compounds which are so unstable as to deleteriously decompose under the reaction conditions employed are not contemplated. The selection of suitable substituents is within the skill of the art or may be established through routine testing. Typical of such substituents include any of the above-listed moieties as well as hydroxy, amidine, amino, sulfonyl, sulfinyl, sulfonate, nitro, phosphate, phosphite, alkali metal mercapto and the like.

The olefinically unsaturated compound is usually one in which each R group which is not hydrogen is independently alkyl, alkenyl or aryl, or (less often) a corresponding substituted radical. Monoolefinic and diolefinic compounds, particularly the former, are preferred, and especially terminal monoolefinic (mono-1-olefins or alpha-olefins) hydrocarbons; that is, those compounds in which $R^5$, $R^6$ and $R^7$ are hydrogen, and $R^4$ is alkyl or aryl, especially alkyl (that is, the olefin is aliphatic). Olefinic compounds having from about 3 to about 70 carbon atoms, preferably from about 8 to 36 carbon atoms and especially from about 8 to about 20 carbon atoms are desirable.

The aliphatic mono-1-olefin or alpha-olefin (i.e., terminal olefin) is one which is unbranched on the olefinic carbon atoms; that is, which contains the moiety $CH_2=CH-$. It also usually contains substantially no branching on the allylic carbon atoms; that is, it preferably contains the moiety $CH_2=CHCH_2-$. Preferred mono-1-olefins or alpha-olefins have about 8 to about 20, preferably about 15 to about 18 carbon atoms. Mixtures of these olefins are commercially available and such mixtures are suitable for use in this invention.

Exemplary of mono-1-olefins or alpha-olefins are 1-octene, 1-nonene, 1-decene, 1-dodecene, 1-tridecene, 1-tetradecene, 1-pentadecene, 1-hexadecene, 1-heptadecene, 1-octadecene, 1-nonadecene, 1-eicosene, 1-henicosene, 1-docosene, 1-tetracosene, 1-pentacosene, 1-hexacosene, 1-octacosene, 1-nonacosene, etc. Exemplary of commercially available alpha olefin mixtures are $C_{15-18}$ alpha-olefins, $C_{12-16}$ alpha-olefins, $C_{14-16}$ alpha-olefins, $C_{14-18}$ alpha-olefins, $C_{16-18}$ alpha-olefins, $C_{16-20}$ alpha olefins, $C_{22-28}$ alpha-olefins, etc. Additionally, $C_{30+}$ alpha-olefin fractions such as those available from Gulf Oil Company under the name Gulftene can be used.

Mono-olefins which are suitable for use in accordance with the present invention can be derived from the cracking of paraffin wax. The wax cracking process yields both even and odd number $C_{6-20}$ liquid olefins of which 85 to 90 percent are straight chain 1-olefins. The balance of the cracked wax olefins is made up of internal olefins, branched olefins, diolefins, aromatics and impurities. Distillation of the $C_{6-20}$ liquid olefins obtained from the wax cracking process yields fractions (i.e., $C_{15-18}$ alpha-olefins) which are particlarly useful in accordance with this invention.

Other mono-olefins can be derived from the ethylene chain growth process. This process yields even numbered straight chain 1-olefins from a controlled Ziegler polymerization.

Other methods for preparing the mono-olefins of this invention include chlorination-dehydrochlorination of paraffins and catalytic dehydrogenation of paraffins.

The above procedures for the preparation of mono-olefins are well known to those of ordinary skill in the art and are described in detail under the heading "Olefins" in the *Encyclopedia of Chemical Technology*, Second Edition, Kirk and Othmer, Supplement, Pages 632–657, Interscience Publishers, Div. of John Wiley and Son, 1971, which is hereby incorporated by reference for its relevant disclosures pertaining to methods for preparing mono-olefins.

Also, fatty acid esters or amides derived from one or more unsaturated carboxylic acids are particularly useful as the olefinically unsaturated compounds.

The term "fatty acid" as used herein refers to acids which may be obtained by hydrolysis of a naturally occurring vegetable or animal fat or oil. These are usually in the $C_{16-20}$ range and include oleic acid, linoleic acid and the like.

Fatty acid amides that are useful include oleamide (sometimes referred to as oleyl amide), N,N-dimethyl oleamide, N,N-bis(2-hydroxyethyl)oleamide, and N,N-di-n-butyl oleamide.

Fatty acid esters which are useful are primarily esters of aliphatic alcohols, including monohydric alcohols such as methanol, ethanol, 1-propanol, 2-propanol, the butanols, etc., and polyhydric alcohols including ethylene glycol, propylene glycol, trimethylene glycol, neopentyl glycol, glycerol and the like. The polyhydric alcohols can be partially or fully esterified. Particularly preferred are fatty oils derived predominantly from unsaturated acids, that is, triglycerides of long chain unsaturated carboxylic acids, especially linoleic and oleic acids. These fatty oils include such naturally occurring animal and vegetable oils as lard oil, peanut oil, cotton seed oil, soybean oil, corn oil, palm oil, sunflower oil, and the like. Mixtures of two or more of these fatty oils can also be used.

The composition and nature of fatty oils is well known to those of ordinary skill in the art and can be found in more detail in M. P. Doss, Properties of the Principal Fats, Fatty Oils, Waxes, Fatty Acids and Their Salts, The Texas Company, 1952, which is hereby incorporated by reference for its description of the fatty oils and unsaturated carboxylic acids useful for this invention.

Mixtures of fatty acid esters and mono-olefins can be used in accordance with the present invention. A particularly preferred mixture is that of $C_{15-18}$ alpha-olefins and soybean oil.

The equivalent weight of component (B) can be determined by dividing its molecular weight by the number of olefinic double bonds (—C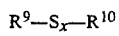C—) present. The number of equivalents of component (B) can be determined by dividing the weight of component (B) by its equivalent weight.

The ratio of equivalents of component (A) to equivalents of component (B) is in the range of about 1000:1 to about 1:5, preferably about 500:1 to about 1:3, more preferably about 100:1 to about 1:3, and more preferably about 50:1 to about 1:3. In a particularly advantageous embodiment, the ratio of equivalents of component (A) to equivalents of component (B) is about 25:1.

Component (C)

The term "active sulfur" is used herein to mean sulfur in a form which can cause staining of copper and similar materials. Standard tests are available to determine sulfur activity. For example, ASTM D 1662 can be used for determination of active sulfur in cutting fluids. Active sulfur can be elemental sulfur, or it can be present in compounds reprsented by the formula $$R^9—S_x—R^{10}$$

wherein $R^9$ and $R^{10}$ are independently hydrogen or organic groups, and x is a number greater than 2, preferably in the range of about 3 to about 15. Component (C) is present either as an impurity resulting generally during the formation of component (A)(I), or as an added ingredient which can be provided for reacting with component (B) or the combination of components (A) and (B) to modify the properties of components (A) and/or (B).

In general, the $R^9$ and $R^{10}$ groups in the above formula which are not hydrogen may be satisfied by such groups as —C$(R^{11})_3$, —CYY$R^{11}$, —CYN$(R^{11})_2$, —CYYN$(R^{11})_4$, —CYYM, —CN, —YM,

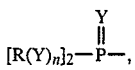

—$R^{11}$, —X, —Y$R^{11}$ or —Ar, wherein:

Each $R^{11}$ is independently hydrogen, alkyl, alkenyl, aryl, substituted alkyl, substituted alkenyl or substituted aryl, with the proviso that any two $R^{11}$ groups can be alkylene or substituted alkylene whereby a ring of up to about 12 atoms is formed;

M is one equivalent of a metal cation (preferably Group I or II, eg. sodium, potassium, barium, calcium);

X is halogen (e.g., chloro, bromo, or iodo);

Y is oxygen or divalent sulfur;

n is zero or one;

Ar is an aryl or substituted aryl radical of up to about 12 carbon atoms in the substituent.

$R^9$ and $R^{10}$ may also together form an alkylene or substituted alkylene group; i.e., an alicyclic group.

The natures of the substituents in the substituted moieties described above are not normally a critical aspect of the invention and any such substituent is useful so long as it is or can be made compatible with lubricant or functional fluid environments and does not interfere under the contemplated reaction conditions. The selection of suitable substituents is within the skill of the art or may be established through routine testing. Typical of such substituents include any of the above-listed moieties as well as hydroxy, amidine, amino, sulfonyl sulfinyl, sulfonate, nitro, phosphate, phosphite, alkali metal mercapto and the like.

When component (C) is in the form of elemental sulfur, its equivalent weight is its atomic weight. When component (C) is in the form,

$$R^9-S_x-R^{10}$$

its equivalent weight is its molecular weight divided by x-2. The number of equivalents of component (C) can be determined by dividing the weight of component (C) by its equivalent weight.

The ratio of equivalents of component (A) to equivalents of component (C) is in the range of about 1:0 to about 1:6. The ratio of equivalents of component (B) to equivalents of component (C) is in the range of about 1:0 to about 1:3. The specification of ratios of (A):(C) and (B):(C) of 1:0 are shorthand methods used herein and in the appended claims of identifying compositions wherein the presence of component (C) as an impurity is anticipated, but the actual levels observed are negligible or non-existent. In a particularly advantageous embodiment wherein component (C) is added for the purpose of modifying the properties of components (A) and/or (B), the ratio of equivalents of component (A) to equivalents of component (B) to equivalents of component (C) is about 1:2:3.

In preparing the compositions of the present invention, the starting material is the acid, i.e., component (A)(I), or mixture of acids, i.e., components (A)(I) and (A)(II). Component (B) is added either at the same time, or prior to, or subsequent to the addition of metal base required for the formation of component (A). Component (C), if present, is present either as an impurity resulting from the formation of component (A)(I), for example, or is added preferably at the same time component (B) is added. By heating the combination of components (A)(B) and (C), substantially all of component (C) reacts with or is consumed by component (B) and/or the combination of components (A) and (B), and the resulting compositions are characterized by relatively low (for example, less than 300 parts per million as measured by IP-155) levels of active sulfur. The term "substantially all" with respect to the consumption of component (C) is used herein to mean that subsequent to the reaction between component (C) and component (B), or the combination of components (A) and (B), the resulting compositions are characterized by sufficiently low levels of active sulfur so as to be non-staining or non-corrosive to copper or similar materials. The reaction temperature is generally in the range of about 80° C. to about 140° C., preferably about 80° C. to about 130° C., more preferably about 100° C. to about 120° C. The resulting compositions are useful, for example, as anti-wear agents and anti-oxidants in lubricants and functional fluids. Lubricants and functional fluids employing these compositions are particularly suitable for applications wherein contact with copper and similar materials is anticipated due to the non-staining, non-corrosive characteristics resulting from the low levels of active sulfur in these compositions.

While not wishing to be bound by theory, it is believed that component (C) reacts with the olefinic double bonds of component (B) and that component (A) acts as a catalyst or promoter. It is possible, however, that, under various circumstances, component (A) also enters into the reaction. In order for the reaction to proceed to completion (i.e., react substantially all of component (C) with component (B) or the combination of components (A) and (B)) at relatively low temperatures (e.g. 80° C. to 140° C.) an effective amount of component (A) to catalyze, promote, or enter into the reaction must be present.

An advantage of the present invention is that active sulfur, i.e., component (C), reacts with or is consumed by component (B) or the combination of components (A) and (B) at relatively low temperatures (e.g., about 80° C. to about 140° C.) in relatively short periods of time to yield useful compositions characterized by relatively low levels of active sulfur and light color. In one embodiment, active sulfur which is present as an impurity resulting from the formation of component (A)(I) is effectively eliminated (or reduced to acceptable levels) from useful metal salts of component (A)(I) or metal salts of mixtures of components (A)(I) and (A)(II). In another embodiment the sulfurization of olefinically unsaturated compounds, i.e., component (B), is enhanced or promoted by component (A), and useful compositions comprising sulfurized reaction products characterized by relatively low levels of active sulfur are obtained.

In all examples, unless otherwise stated, all parts are parts by weight.

EXAMPLE 1

A reaction mixture is prepared by the addition of 3120 parts (24.0 moles) of 2-ethylhexanol and 444 parts (6.0 moles) of isobutyl alcohol. With nitrogen blowing at 1.0 cubic feet per hour, 1540 parts (6.9 moles) of $P_2S_5$ is added to the mixture over a two-hour period while maintaining the temperature at 60°–78° C. The mixture is held at 75° C. for one hour and is stirred an additional two hours while cooling. The mixture is filtered through diatomaceous earth. The filtrate is the product.

EXAMPLE 2

A reaction mixture is prepared by the addition of 590 parts (14.4 moles) of ZnO, 114 parts of a commercially available mixture of $C_{15-18}$ alpha-olefins and 457 parts of diluent oil. At 25° C., 4745 parts (12.5 moles) of the product of Example 1 is added to the mixture over a thirty minute period. The exotherm increases the temperature to 70° C. The mixture is heated to 85° C. and maintained at that temperature for three hours. The mixture is stripped to 110° C. at 25 mm. Hg. The mixture is filtered twice through diatomaceous earth. The filtrate is the product. A 1% solution of this product in mineral oil gives an ASTM D130 copper strip rating of 1A after three hours at 100° C.

EXAMPLE 3

A slurry is prepared by the addition of 440 parts (10.7 equivalents) of ZnO and 300 parts diluent oil. 3254 parts (9.73 equivalents) of O,O-di-(4-methyl-2-pentyl)phosphorodithioic acid is added to the slurry over a 2.5 hour period. The exotherm increases the temperature to 86° C. The mixture is held at 86° C. for three hours. 80 parts (0.35 equivalents) of a commercially available mixture of $C_{15-18}$ alpha-olefins is added to the mixture. The mixture is stripped to 110° C. at 15 mm. Hg. The temperature is increased from 90° C. to 110° C. over a two-hour period. The residue is held at 110° C. under a nitrogen flow of 0.5 cubic feet per hour for an additional two hours before being allowed to cool. The residue is filtered through diatomaceous earth. The filtrate is the product. The level of active sulfur of the product as measured by IP-155 is 39 parts per million.

EXAMPLE 4

A reaction mixture is prepared by the addition of 49 parts (1.2 equivalents) of ZnO over a 15-minute period to 300 parts (1.0 equivalents) of O,O-di(alkyl)phosphorodithioic acid containing 40 percent isopropyl and 60 percent 4-methyl-2-pentyl groups. The exotherm increases the temperature to 70° C. The mixture is heated to 80° C. and maintained at 80° C. for three hours with stirring. The mixture is stripped to 110° C. at 20 mm. Hg. The residue is an intermediate product. 310 parts of intermediate product is mixed with 106 parts (3.31 equivalents) sulfur and 514 parts (2.18 equivalents) of a commercially available mixture of $C_{15-18}$ alpha-olefins. The mixture is heated to 120° C. with stirring and nitrogen blowing beneath the liquid surface at 1.0 cubic feet per hour. The mixture is held at 120° C. with nitrogen blowing at one cubic foot per hour for three hours. A cloth filter pad is packed with five parts diatomaceous earth and ten parts diatomaceous earth is stirred into the mixture. The mixture is vacuum filtered through the cloth pad to provide 879 parts of red-amber liquid. The liquid is refiltered through paper giving 869 parts of red-amber liquid. The filtrate is the product. A 2% solution of this product in mineral oil gives an ASTM D130 copper strip rating of 1A after three hours at 121° C.

EXAMPLE 5

The active sulfur content of a neutral zinc salt of O,O-di-(4-methyl-2-pentyl)phosphorodithioic acid is 2732 parts per million. 1000 parts (2.78 equivalents) of this zinc salt and 31.83 parts (0.139 equivalents) of a commercially available mixture of $C_{15-18}$ alpha-olefins are heated at 110° C. with medium speed stirring for three hours under a nitrogen flow of 0.5 cubic feet per hour. The level of active sulfur of the resulting mixture as measured by IP-155 is 50 parts per million. A 1% solution of this mixture in mineral oil gives an ASTM D130 copper strip rating of 1A after three hours at 100° C. and 1A after three hours at 120° C.

EXAMPLE 6

The active sulfur content of a neutral zinc salt of O,O-di-(4-methyl-2-pentyl)phosphorodithioic acid is 2850 parts per million. 150 parts by weight of this zinc salt and 5.97 parts by weight of a commercially available mixture of $C_{15-18}$ alpha-olefins are heated at 120° C. for three hours under a nitrogen flow of 0.5 cubic feet per hour using medium speed stirring. The level of active sulfur of the resulting mixture as measured by IP-155 is 22 parts per million. A 1% solution of this mixture in mineral oil gives an ASTM D130 copper strip rating of 1A after three hours at 100° C.

EXAMPLE 7

150 parts of the starting zinc salt used in Example 6 and 3 parts of a commercially available mixture of $C_{15-18}$ alpha-olefins are heated at 120° C. for 3 hours under a nitrogen flow of 0.5 cubic feet per hour. The level of active sulfur of the resulting mixture as measured by IP-155 is 36 parts per million.

EXAMPLE 8

150 parts of the starting zinc salt used in Example 6 and 1.5 parts of a commercially available mixture of $C_{15-18}$ alpha-olefins are heated at 120° C. for 3 hours under a nitrogen flow of 0.5 cubic feet per hour. The level of active sulfur of the resulting mixture as measured by IP-155 is 29 parts per million.

EXAMPLE 9

A slurry is prepared by the addition of 486.6 parts (11.86 equivalents) of ZnO and 243.1 parts diluent oil. With medium speed stirring 1204 parts (3.6 equivalents) of O,O-di-(4-methyl-2-pentyl)phosphorodithioic acid are added to the slurry and the temperature of the resulting mixture is increased from 56° C. to 87° C. over a period of 20 minutes. 2407 parts (7.2 equivalents) of O,O-di-(4-methyl-2-pentyl)phosphorodithioic acid are added to the mixture. The temperature of the mixture is maintained at 86° C. for 4 hours. 500 parts of the mixture are poured off. The remaining 3831 parts of mixture are mixed with 156.04 parts of a commercially available mixture of $C_{15-18}$ alpha-olefins. The mixture is stripped to 105° C. at 15 mm. Hg. The temperature of the mixture is increased from 22° C. to 105° C. over a 3½ hour period. The mixture is held at 105° C. under a nitrogen flow of 0.5 cubic feet per hour for an additional two hours before being allowed to cool. The mixture is cooled and filtered through diatomaceous earth. The filtrate is the product. The active sulfur content of the product as measured by IP-155 is 49 parts per million. A 1% solution of this product in mineral oil gives an ASTM D130 copper strip rating of 1A after three hours at 100° C.

EXAMPLE 10

100 parts (0.303 equivalents) of soy bean oil and 46 parts (0.201 equivalents) of a commercially available mixture of $C_{15-18}$ alpha-olefins are mixed for five minutes. A reaction mixture is prepared by the addition of 3 parts of the foregoing soy bean oil/alpha-olefin mixture and 100 parts of a zinc salt of O,O-di(alkyl)phosphorodithioic acid containing 20% butyl and 80% 2-ethylhexyl groups. (The molar ratio of the combination of 2 ethylhexanol and butanol to $P_2S_5$ used in making the O,O-di(alkyl)phosphorodithioic acid is 4.4:1. The ratio of acid to zinc oxide is 1:1.3 equivalents.) The reactants are mixed for ten minutes and heated at 130° C. for four hours.

EXAMPLE 11

Example 10 is repeated with the exception that 6 parts, rather than 3 parts, of the soy bean/$C_{15-18}$ alpha-olefin mixture is reacted with the O,O-di(alkyl)phosphorodithioic acid zinc salt.

EXAMPLE 12

Example 10 is repeated with the exception that 12 parts, rather than 3 parts, of the soy bean oil/$C_{15-18}$ alpha-olefin mixture is reacted with the O,O-di(alkyl)-phosphorodithioic acid zinc salt.

EXAMPLE 13

A reaction mixture of 26.4 parts (0.08 equivalents) of soy bean oil, 11.4 parts (0.05 equivalents) of a commercially available mixture of $C_{15-18}$ alpha-olefins, and 1006 parts (2.60 equivalents) of O,O-di(alkyl)phosphorodithioic acid containing 80% 2-ethylhexyl and 20% isobutyl groups is heated rapidly to 120° C. and maintained at 120°–125° C. for one hour. The mixture is cooled to room temperature. The mixture is added over a 30-minute period to a slurry of 139 parts (3.38 equivalents) of zinc oxide and 121 parts of diluent oil. The exotherm increases the temperature to 60° C. The mixture is heated to 80° C. and maintained at that temperature for three hours. The mixture is stripped to 98° C. at 16 mm. Hg. The mixture is filtered through diatomaceous earth. The filtrate, which is the product, is a clear yellow liquid. A 1% solution of this product in mineral oil gives an ASTM D130 copper strip rating of 1A after three hours at 100° C.

EXAMPLE 14

A reaction mixture is prepared by the addition of 117.9 parts (2.9 equivalents) of zinc oxide, 90.7 parts diluent oil and 22.6 parts of a commercially available mixture of $C_{15-18}$ alpha-olefins. 947.5 parts (2.5 equivalents) of O,O-di(alkyl)phosphorodithioic acid containing 80% isooctyl and 20% isobutyl groups is added to the mixture of a period over a 45 minute period. The exotherm increases the temperature to 55°–60° C. The mixture is heated to 85° C. and maintained at that temperature for three hours. The mixture is stripped to 103° C. at 10 mm. Hg. The mixture is filtered through diatomaceous earth. The filtrate is the product. A 1% solution of this product in mineral oil gives an ASTM D130 copper strip rating of 1A after three hours at 100° C.

EXAMPLE 15

A reaction mixture is prepared by the addition of 141.5 parts (3.45 equivalents) of zinc oxide, 129.0 parts diluent oil, and 23.1 parts of a commercially available mixture of $C_{15-18}$ alpha-olefins. 1015 parts (3.0 equivalents) of O,O-di(alkyl)phosphorodithioic acid containing 60% 2-ethylhexyl and 40% isobutyl groups are added to the mixture over a one hour period. The exotherm increases the temperature to 60° C. The mixture is heated to 80°–85° C. and held at that temperature for three hours. The mixture is cooled to 50° C. The mixture is stripped to 100° C. at 18 mm. Hg. The mixture is filtered through diatomaceous earth. The filtrate is the product. A 1% solution of this product in mineral oil gives an ASTM D130 copper strip rating of 1A after three hours at 100° C.

EXAMPLE 16

A reaction mixture is prepared by the addition of 141.5 parts (3.45 equivalents) zinc oxide, 132.6 parts diluent oil and 24.4 parts of a commercially available mixture of $C_{15-18}$ alpha-olefins. 1097.8 (3.0 equivalents) of O,O-di(alkyl)phosphorodithioic acid containing 40% 2-ethylhexyl and 60% isobutyl groups are added to the mixture over a one hour period while heating to 70° C. The mixture is held at 70°–75° C. for three hours. The mixture is cooled. The mixture is stripped to 100° C. at 15 mm. Hg. The mixture is filtered twice through diatomaceous earth. The filtrate is the product. A 1% solution of this product in mineral oil gives an ASTM D130 copper strip rating of 1A after three hours at 100° C.

EXAMPLE 17

261 parts (0.98 equivalents) of O,O-di(alkyl)phosphorodithioic acid containing 50% n-butyl and 50% isopropyl groups are added to 48 parts (1.17 equivalents) of zinc oxide over a one-half hour period. The exotherm increases the temperature to 50° C. The mixture is heated to 80° C. and maintained at that temperature for three hours. The mixture is stripped to 110° C. at 10 mm. Hg. 25 parts (0.78 equivalents) of sulfur and 125 parts (0.53 equivalents) of a commercially available mixture of $C_{15-18}$ alpha-olefins are added to the mixture. The mixture is heated to 120° C. and maintained at that temperature for three hours. The mixture is filtered through diatomaceous earth. The filtrate, which is the product, is a brown liquid. A 1% solution of this product in mineral oil gives an ASTM D130 copper strip rating of 1A after three hours at 100° C.

EXAMPLE 18

A reaction mixture of 263 parts of a neutral zinc salt of O,O-di-(4-methyl-2-pentyl)phosphorodithioic acid, 67 parts (2.1 equivalents) of sulfur, and 196 parts (1.4 equivalents) of 1-decene is heated to 100° C. and maintained at that temperature for three hours. The mixture is heated to 110° C. and maintained at that temperature for three hours. The mixture is stripped to 106° C. at 18 mm. Hg. The mixture is filtered through a pad of diatomaceous earth. The filtrate, which is the product, is a clear brown liquid. A 2% solution of this product in mineral oil gives an ASTM D130 copper strip rating of 1A after three hours at 100° C.

EXAMPLE 19

As a comparative example, 196 parts (1.4 equivalents) of 1-decene and 67 parts (2.1 equivalents) of sulfur are heated to 130° C. After maintaining the temperature of the mixture at 130° C. for three hours, the mixture is cooled and sulfur is precipitated. The color of the liquid is light orange. The mixture is heated to 130° C. and maintained at that temperature for six hours. The mixture has a darker color. Sulfur precipitates when the mixture is cooled. The mixture is heated to 130° C. and maintained at that temperature for three hours. The mixture is cooled and 46 parts of sulfur are collected and washed with solvent.

EXAMPLE 20

A reaction mixture of 376 parts of a neutral zinc salt of O,O-di-(alkyl)phosphorodithioic acid containing 40% isopropyl and 60% 4-methyl-2-pentyl groups, 140 parts 1-decene (4.0 equivalents) and 192 parts (6.0 equivalents) sulfur are heated to 100° C. and maintained at that temperature for three hours. Sulfur precipitates upon cooling. The mixture is maintained at 100° C. for three additional hours. Sulfur precipitates upon cooling. The mixture is heated to 100° C. and maintained at that temperature for 23 hours. A 1.5% solution of this mixture in mineral oil gives an ASTM D130 copper strip rating of 1B after three hours at 100° C. The mixture is stripped to 110° C. at 25 mm. Hg. The mixture is then stripped to 86° C. at 0.2 mm. Hg. The mixture is filtered through diatomaceous earth. The filtrate, which is the product, is a clear brown liquid.

EXAMPLE 21

A reaction mixture is prepared by the addition of 296 parts of a neutral zinc salt of O,O-di(alkyl)phosphorodithioic acid containing 40% isopropyl and 60% 4-methyl-2-pentyl groups, 210 parts 1-decene (1.5 equivalents) and 86 parts (2.7 equivalents) of sulfur. The mixture is heated to 110° C. and maintained at that temperature for six hours. The mixture is stripped to 110° C. at 22 mm. Hg. The mixture is filtered through a pad of diatomaceous earth. The filtrate which is the product is a clear brown liquid. A 2% solution of this product in mineral oil gives an ASTM D130 copper strip rating of 1A after three hours at 100° C.

EXAMPLE 22

A reaction mixture is prepared by the addition of 263 parts of a neutral zinc salt of O,O-di(alkyl)phosphorodithioic acid containing 40% isopropyl and 60% 4-methyl-2-pentyl groups, 196 parts (1.4 equivalents) of 1-decene, and 67 parts (2.1 equivalents) of sulfur. The mixture is heated to 90° C. and maintained at that temperature for three hours. Sulfur precipitates from the mixture. The mixture is heated to 100° C. and maintained at that temperature for three hours. The mixture is stripped to 100° C. at 13 mm. Hg. The mixture is filtered through diatomaceous earth. The filtrate, which is the product, is a clear brown liquid. A 2% solution of this product in mineral oil gives an ASTM D130 copper strip rating of 1A after three hours at 100° C.

EXAMPLE 23

A reaction mixture is prepared by the addition of 286 parts (0.78 equivalents) of a neutral zinc salt of O,O-di(4-methyl-2-pentyl)phosphorodithioic acid, 252 parts (0.78 equivalents) of a neutral zinc salt of O,O-di(alkyl)-phosphorodithioic acid containing 40% isopropyl and 60% 4-methyl-2-pentyl groups, 490 parts (3.5 equivalents) of 1-decene, and 168 parts (5.25 equivalents) of sulfur. The mixture is heated to 110° C. and maintained at that temperature for six hours. The mixture is stripped to 108° C. at 20 mm. Hg. The mixture is filtered through a pad of diatomaceous earth. The filtrate, which is the product, is a clear red liquid. A 2% solution of this product in mineral oil gives an ASTM D130 copper strip rating of 1A after three hours at 100° C.

EXAMPLE 24

Part A: 1000 parts by weight of a neutral zinc salt of O,O-di(4-methyl-2-pentyl)phosphorodithioic acid is reacted with 34 parts by weight of propylene oxide at 80°–85° C. The mixture is blown with nitrogen at 85° C. and 100 mm. Hg. The mixture is filtered. The filtrate is the product.

Part B: A reaction mixture is prepared by the addition of 263 parts of the product of Part A, 196 parts (1.4 equivalents) of 1-decene, and 67 parts (2.1 equivalents) of sulfur. The mixture is heated to 110° C. and maintained at that temperature for six hours. The mixture is stripped to 110° C. at 21 mm. Hg. The mixture is filtered through a pad of diatomaceous earth. The filtrate, which is the product, is a clear brown liquid. A 2% solution of this product in mineral oil gives an ASTM D130 copper strip rating of 1A after three hours at 100° C.

EXAMPLE 25

A reaction mixture is prepared by the addition of 168 parts of a neutral zinc salt of O,O-di(alkyl)phosphorodithioic acid containing 40% isopropyl and 60% 4-methyl-2-pentyl groups, 200 parts soy bean oil, 91 parts of a commercially available mixture of $C_{15-18}$ alpha-olefins, 11 parts of Sylfat 96 (a commercially available tall oil acid available from Sylvia Chemical) and 34 parts sulfur. The mixture is heated to 110° C. and maintained at that temperature for three hours. The mixture is filtered through a pad of diatomaceous earth. The filtrate, which is the product, is a clear amber-red liquid. A 1.5% solution of this product in mineral oil gives an ASTM D130 rating of 1A after three hours at 100° C.

EXAMPLE 26

A reaction mixture is prepared by the addition of 413 parts of a neutral zinc salt of O,O-di(alkyl)phosphorodithioic acid containing 40% isopropyl and 60% 4-methyl-2-pentyl groups, 281 parts of Armid O, (a commercially available product of Armak Corporation identified as an oleyl amide), and 32 parts sulfur are heated to 110° C. and maintained at that temperature for three hours. The mixture is filtered through a pad of diatomaceous earth. The filtrate, which is the product, is a brown wax.

EXAMPLE 27

A reaction is prepared by the addition of 168 parts of a neutral zinc salt of O,O-di(4-methyl-2-pentyl)phosphorodithioic acid, 200 parts soy bean oil, 91 parts of a commercially available mixture of $C_{15-18}$ alpha-olefins, 11 parts of Sylfat 96, and 34 parts sulfur. The mixture is heated to 120° C. and maintained at that temperature for three hours. The mixture is filtered through diatomaceous earth. The filtrate, which is the product, is a clear brown liquid. A 1.5% solution of this product in mineral oil gives an ASTM D130 rating of 1A after three hours at 100° C.

EXAMPLE 28

A reaction mixture is prepared by the addition of 321 parts of a neutral zinc salt of O,O-di(alkyl)phosphorodithioic acid containing 65% isobutyl and 35% primary amyl groups, 19 parts zinc oxide, 400 parts soy bean oil, 184 parts of a commercially available mixture of $C_{15-18}$ alpha-olefins, and 58 parts sulfur. The mixture is heated to 130° C. The exotherm increases the temperature to 135° C. The mixture is cooled to 130° C. and maintained at that temperature for three hours. The mixture is filtered through a pad of diatomaceous earth. The filtrate, which is the product, is a clear brown liquid. A 1.5% solution of this product in mineral oil gives an ASTM D130 rating of 1A after three hours at 100° C.

EXAMPLE 29

A reaction mixture is prepared by the addition of 315 parts of a neutral zinc salt of O,O-di-(2-ethylhexyl)phosphorodithioic acid, 200 parts soy bean oil, 86 parts of a commercially available mixture of $C_{15-18}$ alpha-olefins, and 29 parts sulfur. The mixture is heated to 130° C. and maintained at that temperature for three hours. The mixture is filtered through pads of diatomaceous earth. The filtrate, which is the product, is a clear brown liquid. A 2% solution of this product in mineral oil has an ASTM D130 copper strip rating of 1A after three hours at 100° C.

EXAMPLE 30

A reaction mixture is prepared by the addition of 263 parts of a neutral zinc salt of O,O-di-(2-ethylhexyl)phosphorodithioic acid, 10 parts zinc oxide, and 196 parts of 1-decene. The mixture is heated to 130° C. 67 parts of sulfur is added to the mixture. The mixture is maintained at 130° C. for six hours. The mixture is filtered through a pad of diatomaceous earth. The filtrate, which is the product, is a clear brown-red liquid. A 2% solution of this product has an ASTM D130 copper strip rating of 1A after three hours at 100° C.

EXAMPLE 31

A reaction mixture is prepared by the addition of 608 parts of a neutral zinc salt of O,O-di-(isooctyl)phosphorodithioic acid, 224 parts (2.0 equivalents) of 1-octene, and 80 parts (2.5 equivalents) of sulfur. The reaction mixture is heated to 110° C. and maintained at a temperature for three hours with nitrogen blowing at a rate of 0.5 cubic feet per hour. The mixture is stripped to 110° C. at 10 mm. Hg. The mixture is filtered through a diatomaceous earth. The filtrate, which is the product, is a brown-reddish liquid. A 2% solution of this product has an ASTM D130 copper strip rating of 1A after three hours at 100° C.

EXAMPLE 32

A reaction mixture is prepared by the addition of 495 parts (0.910 equivalents) of a neutral zinc salt of O,O-di-(2-ethylhexyl)phosphorodithioic acid, and three parts (0.0216 equivalents) of 1-decene. The mixture is heated to 120° C. and maintained at that temperature for four hours. The mixture is filtered. The filtrate, which is the product, is a golden transparent liquid. A 2% solution of this product in mineral oil has an ASTM D130 copper strip rating of 1A after three hours at 100° C.

EXAMPLE 33

A reaction mixture is prepared by the addition of 495 parts of a neutral zinc salt of O,O-di-(2-ethylhexyl)phosphorodithioic acid, and five parts of a commercially available mixture of $C_{15-18}$ alpha-olefins. The mixture is heated to 120° C. and maintained at that temperature for two hours. The mixture is filtered through filter paper. The filtrate is the product. A 1% solution of this product in mineral oil has an ASTM D130 copper strip rating of 1A after three hours at 100° C.

EXAMPLE 34

A reaction mixture is prepared by the addition of 480 parts of a neutral zinc salt of O,O-di-(2-ethylhexyl)phosphorodithioic acid, and 20 parts of a commercially available mixture of $C_{15-18}$ alpha-olefins. The mixture is heated to 100° C. and maintained at that temperature for five hours. The mixture is filtered through filter paper. The filtrate is the product. A 1% solution of this product in mineral oil has an ASTM D130 copper strip rating of 2A after three hours at 100° C.

EXAMPLE 35

A slurry is provided by the addition of 180 parts (4.39 equivalents) of zinc oxide, and 134 parts diluent oil. To this slurry is added a mixture of 1123 parts (2.70 equivalents) of O,O-di-(2-ethylhexyl)phosphorodithioic acid and 97 parts (0.67 equivalents) of 2-ethyl hexanoic acid over a 45-minute period with stirring. The exotherm increases the temperature to 55° C. The mixture is heated to 80°–90° C. and maintained at that temperature for three hours. The mixture is stripped to 115° C. at 4 mm. Hg. To this mixture is added a mixture of 154 parts (4.81 equivalents) of sulfur and 577 parts (3.17 equivalents) of a commercially available Diels-Alder butadiene/butyl acrylate (1:1 molar ratio) adduct. The mixture is heated to 110° C. and maintained at that temperature for 12 hours. The mixture is stripped to 110° C. at 4 mm. Hg. Diatomaceous earth is stirred into the mixture and the mixture is vacuum filtered through a cloth pad with diatomaceous earth on the pad. The filtrate, which is the product, is a clear amber liquid. A 1% solution of this product in mineral oil has an ASTM D130 copper strip rating of 1A after three hours at 100° C.

EXAMPLE 36

A reaction mixture is prepared by the addition of 500 parts of a neutral zinc salt of O,O-di-(alkyl)phosphorodithioic acid containing 40% isopropyl and 60% 4-methyl-2-pentyl groups, 150 parts (4.69 equivalents) of sulfur and 350 parts (3.12 equivalents) of 1-octene. The mixture is heated to 110° C. and maintained at that temperature for three hours with nitrogen blowing at 0.5 cubic feet per hour. The mixture is vacuum stripped to 110° C. at 5 mm. Hg. Diatomaceous earth is stirred in the mixture and the mixture is vacuum filtered through cloth with diatomaceous earth on the cloth. The filtrate, which is the product, is a clear amber-brown liquid.

EXAMPLE 37

A reaction mixture is prepared by the addition of 250 parts of a neutral zinc salt of O,O-di(alkyl)phosphorodithioic acid containing 40% isopropyl and 60% 4-methyl-2-pentyl groups, 75 parts (2.34 equivalents) of sulfur and 175 parts (1.56 equivalents) of 2-octene. The mixture is heated to 110° C. and maintained at that temperature for six hours. The mixture is stripped to 110° C. at 25 mm. Hg. Ten parts diatomaceous earth are stirred into the mixture which is cooled and filtered through a cloth pad with diatomaceous earth on the pad. The filtrate, which is the product, is a clear amber-brown liquid. A 2% solution of this product in mineral oil has an ASTM D130 copper strip rating of 1A after three hours at 100° C.

EXAMPLE 38

A reaction mixture is prepared by the addition of 500 parts of a neutral zinc salt of O,O-di(alkyl)phosphorodithioic acid containing 40% isopropyl and 60% 4-methyl-2-pentyl groups, 342 parts (3.29 equivalents) of styrene, and 158 parts (4.94 equivalents) of sulfur. The mixture is heated to 110° C. and maintained at that temperature for six hours. The mixture is stripped to 110° C. at 22 mm. Hg. Ten grams of diatomaceous earth are stirred into the mixture and the mixture is vacuum filtered through a cloth pad having diatomaceous earth on the pad. The filtrate, which is the product, is an opaque, tan, gel-like material. A 1% solution of this product in mineral oil has an ASTM D130 copper strip rating of 1A after three hours at 100° C.

EXAMPLE 39

A slurry is prepared by the addition of 117.2 parts (2.86 equivalents) of zinc oxide and 94.7 parts diluent oil. With medium stirring at a temperature of 22° C., 818 parts (2 equivalents) of O,O-di-(2-ethylhexyl)phosphorodithioic acid, and 12 parts (0.2 equivalents) of acetic acid are added to the slurry over a ten-minute period. The exotherm increases the temperature of the resulting mixture to 61° C. The mixture is heated to 80° C. and maintained at that temperature for three hours. Sixteen parts of 50% sodium hydroxide is added to the mixture. The mixture is stripped to 100° C. at 11 mm. Hg. 22.9 parts (0.1 equivalents) of a commercially available $C_{15-18}$ alpha-olefin mixture is added to the mixture. The mixture is heated to 120° C. and maintained at that temperature for three hours. The mixture is filtered through diatomaceous earth. The filtrate is the product. A 1% solution of this product in mineral oil has an ASTM D130 copper strip rating of 1A after three hours at 100° C.

EXAMPLE 40

A slurry is prepared by the addition of 133.2 parts (3.25 equivalents) of zinc oxide and 98 parts diluent oil. At a temperature of 22° C., 818 parts (2 equivalents) of O,O-di-(2-ethylhexyl)phosphorodithioic acid, and 30 parts (0.5 equivalents) of acetic acid are added to the slurry. The exotherm of the resulting mixture increases the temperature to 60° C. The mixture is heated to 80° C. and maintained at that temperature for three hours. While the mixture is cooling, 40 parts of a 50% sodium hydroxide solution is added to the mixture. The mixture is cooled to 50° C. with stirring. The mixture is stripped to 100° C. at 11 mm. Hg. 22.9 parts (0.1 equivalents) of $C_{16}$ alpha-olefin is added to the mixture. The mixture is heated to 120° C. and maintained at that temperature for three hours. The mixture is filtered through diatomaceous earth. The filtrate is the product. A 1% solution of this product in mineral oil has an ASTM D130 copper strip rating of 1A after three hours at 100° C.

EXAMPLE 41

A slurry is prepared by the addition of 175.89 parts (4.29 equivalents) of zinc oxide and 145.9 parts of diluent oil. To this slurry is added 1245.8 parts (3 equivalents) of O,O-di-(isooctyl)phosphorodithioic acid, and 43.26 parts (0.3 equivalents) of 2-ethylhexanoic acid with stirring at room temperature. The temperature of the mixture is increased to 80° C. and maintained at that level for three hours. The mixture is stripped to 110° C. at 18 mm. Hg. The mixture is cooled to room temperature. 35.4 parts (0.15 equivalents) of a commercially available mixture of $C_{15-18}$ alpha-olefins is added to the mixture. The temperature of the mixture is increased to 130° C. and maintained at that level for three hours. The mixture is filtered through diatomaceous earth. The filtrate, which is the product, is a clear golden liquid. A 1% solution of this product in mineral oil has an ASTM D130 copper strip rating of 1A after three hours at 100° C.

EXAMPLE 42

A slurry is prepared by the addition of 121.8 parts (2.97 equivalents) of zinc oxide and 106.8 parts of diluent oil. With stirring at room temperature, 879.5 parts (2 equivalents) of O,O-di-(isooctyl)phosphorodithioic acid, and 42 parts (0.285 equivalents) of 2-ethylhexanoic acid are added to the slurry. The resulting mixture is heated to 80° C. and maintained at that temperature for three hours. The mixture is stripped to 100° C. at 26 mm. Hg. The mixture is filtered through diatomaceous earth. The filtrate, which is the product, is a golden brown liquid. A 1% solution of this product in mineral oil has an ASTM D130 copper strip rating of 1A after three hours at 100° C.

The compositions of the present invention can be admixed, for example, with a diluent to form a concentrate as discussed below, or with a lubricant or functional fluid, as discussed below.

As previously indicated, the compositions of the present invention are useful as additives for lubricants and functional fluids. They can be employed in a variety of lubricants based on diverse oils of lubricating viscosity, including natural and synthetic lubricating oils and mixtures thereof. The lubricants include crankcase lubricating oils for spark-ignited and compression-ignited internal combustion engines, including automobile and truck engines, two-cycle engines, aviation piston engines, marine and railroad diesel engines, and the like. Also contemplated are lubricants for gas engines, stationary power engines and turbines and the like. Transaxle lubricants, gear lubricants, metal-working lubricants and other lubricating oil and grease compositions, as well as functional fluids such as hydraulic fluids and automatic transmission fluids, benefit from the incorporation therein of the compositions of the present invention.

Natural oils include animal oils and vegetable oils (e.g., castor oil, lard oil) as well as liquid petroleum oils and solvent-treated or acid-treated mineral lubricating oils of the paraffinic, naphthenic or mixed paraffinic-naphthenic types. Oils of lubricating viscosity derived from coal or shale oil can also be included as the base oil. Synthetic lubricating oils include hydrocarbon oils and halosubstituted hydrocarbon oils such as polymerized and interpolymerized olefins (e.g., polybutylenes, polypropylenes, propylene-isobutylene copolymers, chlorinated polybutylenes, etc.); poly(1-hexenes), poly(1-octenes), poly(1-decenes), etc. and mixtures thereof; alkylbenzenes (e.g., dodecylbenzenes, tetradecylbenzenes, dinonylbenzenes, di(2-ethylhexyl)benzenes, etc.); polyphenyls (e.g., biphenyls, terphenyls, alkylated polyphenyls, etc.); alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc. constitute another class of known synthetic oils. These are exemplified by the oils prepared through polymerization of ethylene oxide or propylene oxide, the alkyl and aryl ethers of these polyoxyalkylene polymers (e.g. methylpolyisopropylene glycol ether having an average molecular weight of 1000, diphenyl ether of polyethylene glycol having a molecular weight of 500–1000, diethyl ether of polypropylene glycol having a molecular weight of 1000–1500, etc.) or mono- and polycarboxylic esters thereof, for example, the acetic acid esters, mixed $C_3$–$C_8$ fatty acid esters, or the $C_{13}$ Oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.). Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid, and the like.

Esters useful as synthetic oils also include those made from $C_5$ to $C_{12}$ monocarboxylic acids and polyols and polyol ethers such as neopentyl glycol, trimethylolpropane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another class of synthetic oils (e.g., tetraethyl silicate, tetraisopropyl silicate, tetra-(2-ethylhexyl)silicate, tetra-(4-methyl-2-ethylhexyl)silicate, tetra-(p-tert-butylphenyl)silicate, hexa-(4-methyl-2-pentoxy)-disiloxane, poly(methyl)siloxanes, poly(methylphenyl)-siloxanes, etc.). Other synthetic oils include liquid esters of phosphorus-containing acids (e.g., tricresyl phosphate, trioctyl phosphate, diethyl ester of decylphosphonic acid, etc.), polymeric tetrahydrofurans and the like.

Unrefined, refined and rerefined oils (and mixtures of each with each other) of the type disclosed hereinabove can be used in the lubricants and functional fluids of the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be an unrefined oil. Refined oils are similar to the unrefined oils except they have been further treated in one or more purification steps to improve one or more properties. Many such purification techniques are known to those of skill in the art such as solvent extraction, acid or base extraction, filtration, percolation, etc. Rerefined oils are obtained by processes similar to those used to obtain refined oils applied to refined oils which have been already used in service. Such rerefined oils are also known as reclaimed or reprocessed oils and often are additionally processed by techniques directed to removal of spent additives and oil breakdown products.

Generally, the lubricants and functional fluids of the present invention contain an amount of the compositions of this invention sufficient to provide it with antioxidant and/or anti-wear properties. Normally this amount will be about 0.25% to about 10%, preferably about 0.4% to about 7.5%, of the total weight of the fluid.

The invention also contemplates the use of other additives in combination with the compositions of this invention. Such additives include, for example, detergents and dispersants of the ash-producing or ashless type, corrosion- and auxiliary oxidation-inhibiting agents, pour point depressing agents, auxiliary extreme pressure agents, color stabilizers and anti-foam agents.

The ash-producing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt" is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature above 50° C. and filtering the resulting mass. The use of a "promoter" in the neutralization step to aid the incorporation of a large excess of metal likewise is known. Examples of compounds useful as the promoter include phenolic substances such as phenol, naphthol, alkylphenol, thiophenol, sulfurized alkylphenol, and condensation products of formaldehyde with a phenolic substance; alcohols such as methanol, 2-propanol, octyl alcohol, cellosolve, carbitol, ethylene glycol, stearyl alcohol, and cyclohexyl alcohol; and amines such as aniline, phenylenediamine, phenothiazine, phenyl-beta-naphthylamine, and dodecylamine. A particularly effective method for preparing the basic salts comprises mixing an acid with an excess of a basic alkaline earth metal neutralizing agent and at least one alcohol promoter, and carbonating the mixture at an elevated temperature such as 60°-200° C.

Ashless detergents and dispersants are so called despite the fact that, depending on its constitution, the dispersant may upon combustion yield a non-volatile material such as boric oxide or phosphorus pentoxide; however, it does not ordinarily contain metal and therefore does not yield a metal-containing ash on combustion. Many types are known in the art, and any of them are suitable for use in the lubricants of this invention. The following are illustrative:

(1) Reaction products of carboxylic acids (or derivatives thereof) containing at least about 34 and preferably at least about 54 carbon atoms with nitrogen-containing compounds such as amine, organic hydroxy compounds such as phenols and alcohols, and/or basic inorganic materials. Examples of these "carboxylic dispersants" are described in British Pat. No. 1,306,529 and in many U.S. patents including the following:

| | | |
|---|---|---|
| 3,163,603 | 3,351,552 | 3,541,012 |
| 3,184,474 | 3,381,022 | 3,542,678 |
| 3,215,707 | 3,399,141 | 3,542,680 |
| 3,219,666 | 3,415,750 | 3,567,637 |
| 3,271,310 | 3,433,744 | 3,574,101 |
| 3,272,746 | 3,444,170 | 3,576,743 |
| 3,281,357 | 3,448,048 | 3,630,904 |
| 3,306,908 | 3,448,049 | 3,632,510 |
| 3,311,558 | 3,451,933 | 3,632,511 |
| 3,316,177 | 3,454,607 | 3,697,428 |
| 3,340,281 | 3,467,668 | 3,725,441 |
| 3,341,542 | 3,501,405 | Re 26,433 |
| 3,346,493 | 3,522,179 | |

(2) Reaction products of relatively high molecular weight aliphatic or alicyclic halides with amines, preferably polyalkylene polyamines. These may be characterized as "amine dispersants" and examples thereof are described for example, in the following U.S. patents:

| | |
|---|---|
| 3,275,554 | 3,454,555 |

-continued

| | |
|---|---|
| 3,438,757 | 3,565,804 |

(3) Reaction products of alkyl phenols in which the alkyl group contains at least about 30 carbon atoms with aldehydes (especially formaldehyde) and amines (especially polyalkylene polyamines), which may be characterized as "Mannich dispersants". The materials described in the following U.S. patents are illustrative:

| | |
|---|---|
| 3,413,347 | 3,725,480 |
| 3,697,574 | 3,726,882 |
| 3,725,277 | |

(4) Products obtained by post-treating the carboxylic, amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of his kind are described in the following U.S. patents:

| | | | |
|---|---|---|---|
| 3,036,003 | 3,282,955 | 3,493,520 | 3,639,242 |
| 3,087,936 | 3,312,619 | 3,502,677 | 3,649,229 |
| 3,200,107 | 3,366,569 | 3,513,093 | 3,649,659 |
| 3,216,936 | 3,367,943 | 3,533,945 | 3,658,836 |
| 3,254,025 | 3,373,111 | 3,539,633 | 3,697,574 |
| 3,256,185 | 3,403,102 | 3,573,010 | 3,702,757 |
| 3,278,550 | 3,442,808 | 3,579,450 | 3,703,536 |
| 3,280,234 | 3,455,831 | 3,591,598 | 3,704,308 |
| 3,281,428 | 3,455,832 | 3,600,372 | 3,708,522 |

(5) Interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates. These may be characterized as "polymeric dispersants" and examples thereof are disclosed in the following U.S. patents:

| | |
|---|---|
| 3,329,658 | 3,666,730 |
| 3,449,250 | 3,687,849 |
| 3,519,565 | 3,702,300 |

The above-noted patents are incorporated by reference herein for their disclosures of ashless dispersants.

Auxiliary extreme pressure agents and corrosion- and auxiliary oxidation-inhibiting agents are exemplified by chlorinated aliphatic hydrocarbons such as chlorinated wax; organic sulfides and polysulfides such as benzyl disulfide, bi(chlorobenzyl)disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate; phosphorus esters including principally dihydrocarbon and trihydrocarbon phosphites such as dibutyl phosphite, diheptyl phosphite, dicyclohexyl phosphite, pentylphenyl phosphite, dipentylphenyl phosphite, tridecyl phosphite, distearyl phosphite, dimethyl naphthyl phosphite, oleyl 4-pentylphenyl phosphite, poly-propylene (molecular weight 500)-substituted phenyl phosphite, diisobutyl-substituted phenyl phosphite; and metal thiocarbamates, such as zinc dioctyldithiocarbamate and barium heptylphenyl dithiocarbamate.

The compositions of this invention can be added directly to the lubricant or functional fluid. Often, however, they can be diluted with a substantially inert, normally liquid organic diluent such as mineral oil, naphtha, benzene, toluene or xylene, to form an additive concentrate. These concentrates usually contain from about 20% to about 90% by weight of the composition of this invention and may contain, in addition, one or more other additives known in the art or described hereinabove.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

I claim:

1. A composition comprising:
   (A) a metal salt of (A)(I) at least one acid of the formula

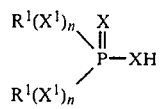

wherein each X and $X^1$ is independently oxygen or sulfur, each n is zero or one, and each $R^1$ is independently the same or different hydrocarbon based group, and (A)(II) at least one carboxylic acid of about 2 to about 40 carbon atoms, the ratio of equivalents of (A)(I) to equivalents of (A)(II) being in the range of about 0.5:1 to about 1:0; and
   (B) an olefinically unsaturated compound capable of reacting with active sulfur, the ratio of equivalents of component (A) to equivalents of component (B) being in the range of about 1000:1 to about 1:5.

2. The composition of claim 1 wherein the ratio of equivalents of (A) to equivalents of (B) is in the range of about 500:1 to about 1:3.

3. The composition of claim 1 wherein the ratio of equivalents of (A) to equivalents of (B) is in the range of about 100:1 to about 1:3.

4. The composition of claim 1 wherein the ratio of equivalents of (A) to equivalents of (B) is in the range of about 50:1 to about 1:3.

5. The composition of claim 1 wherein the ratio of equivalents of (A) to equivalents of (B) is about 25:1.

6. The composition of claim 1 wherein the ratio of equivalents of (A)(I) to equivalents of (A)(II) is in the range of about 0.5:1 to about 500:1.

7. The composition of claim 1 wherein the ratio of equivalents of (A)(I) to equivalents of (A)(II) is in the range of about 0.5:1 to about 200:1.

8. The composition of claim 1 wherein the ratio of equivalents of (A)(I) to equivalents of (A)(II) is in the range of about 0.5:1 to about 100:1.

9. The composition of claim 1 wherein the ratio of equivalents of (A)(I) to equivalents of (A)(II) is in the range of about 0.5:1 to about 50:1, component (A)(II) having more than about three carbon atoms.

10. The composition of claim 1 wherein the ratio of equivalents of (A)(I) to equivalents of (A)(II) is in the range of about 400:1 to about 50:1, component (A)(II) having about three carbon atoms or less.

11. The composition of claim 1 wherein the metal for component (A) is at least one of Group I metals, Group II metals, aluminum, tin, cobalt, lead, zinc, manganese, nickel or a mixture thereof.

12. The composition of claim 1 wherein the metal for component (A) is zinc.

13. The composition of claim 1 wherein each $R^1$ is a hydrocarbon-based group of about 1 to about 50 carbon atoms.

14. The composition of claim 1 wherein each $R^1$ is a hydrocarbon-based group of about 1 to about 30 carbon atoms.

15. The composition of claim 1 wherein each $R^1$ is a hydrocarbon-based group of about 3 to about 18 carbon atoms.

16. The composition of claim 1 wherein each $R^1$ is a hydrocarbon-based group of about 4 to about 8 carbon atoms.

17. The composition of claim 1 wherein component (A)(I) has the formula

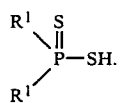

18. The composition of claim 1 wherein component (A)(I) has the formula

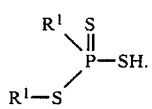

19. The composition of claim 1 wherein component (A)(I) has the formula

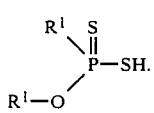

20. The composition of claim 1 wherein component (A)(I) has the formula

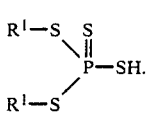

21. The composition of claim 1 wherein component (A)(I) has the formula

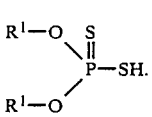

22. The composition of claim 1 wherein component (A)(I) has the formula

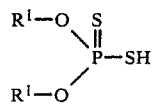

wherein each $R^1$ is the same.

23. The composition of claim 1 wherein component (A)(I) has the formula

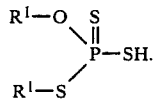

24. The composition of claim 1 wherein component (A) is a zinc salt of a di-(alkyl)phosphorodithioic acid wherein each alkyl has independently from 4 to 8 carbons.

25. The composition of claim 1 wherein component (A)(II) has about 2 to about 20 carbon atoms.

26. The composition of claim 1 wherein component (A)(II) is a monocarboxylic acid.

27. The composition of claim 1 wherein component (A)(II) is a dicarboxylic acid.

28. The composition of claim 1 wherein component (A)(II) is a tricarboxylic acid.

29. The composition of claim 1 wherein component (A)(II) has the formula $R^3COOH$, wherein $R^3$ is an aliphatic or alicyclic hydrocarbon-based group.

30. The composition of claim 1 wherein component (A) has from about 80% to about 200% of the metal present in the corresponding neutral salt.

31. The composition of claim 1 wherein component (A) has from about 100% to about 150% of the metal present in the corresponding neutral salt.

32. The composition of claim 1 wherein component (A) has from about 100% to about 135% of the metal present in the corresponding neutral salt.

33. The composition of claim 1 wherein component (A) has about 103% to about 110% of the metal present in the corresponding neutral salt.

34. The composition of claim 1 wherein component (B) has about 3 to about 70 carbon atoms.

35. The composition of claim 1 wherein component (B) has the formula $$R^4R^5C=CR^6R^7$$

wherein each $R^4$, $R^5$, $R^6$ and $R^7$ is independently hydrogen or an organic group.

36. The composition of claim 1 wherein component (B) is at least one monoolefinic or diolefinic compound.

37. A composition comprising:
(A) a metal salt of (A)(I) at least one acid of the formula

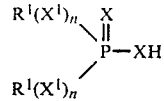

wherein each X and $X^1$ is independently oxygen or sulfur, each n is zero or one, and each $R^1$ is independently the same or different hydrocarbon based group, and (A)(II) at least one carboxylic acid of about 2 to about 40 carbon atoms, the ratio of equivalents of (A)(I) to equivalents of (A)(II) being in the range of about 0.5:1 to about 1:0; and (B) a mono-olefin or a polyolefin capable of reacting with active sulfur, the ratio of equivalents of component (A) to equivalents of component (B) being in the range of about 1000:1 to about 1:5.

38. The composition of claim 37 wherein component (B) is mono-olefin.

39. The composition of claim 37 wherein component (B) is a mono-1-olefin.

40. The composition of claim 37 wherein component (B) is a polyolefin.

41. The composition of claim 37 wherein component (B) is one or more mono-1-olefins about 8 to about 36 carbons.

42. The composition of claim 37 wherein component (B) is one or more mono-1-olefins of about 8 to about 20 carbon atoms.

43. The composition of claim 37 wherein component (B) is one or more mono-1-olefins of about 15 to about 18 carbon atoms.

44. The composition of claim 37 wherein component (B) is selected from the group consisting of one or more of the following alpha-olefin fractions: $C_{15-18}$ alpha-olefins; $C_{12-16}$ alpha-olefins; $C_{14-16}$ alpha-olefins; $C_{14-18}$ alpha-olefins; $C_{16-18}$ alpha-olefins; $C_{16-20}$ alpha-olefins; $C_{22-28}$ alpha-olefins; and $C_{30+}$ alpha-olefins.

45. An additive concentrate comprising a substantially inert, normally liquid organic diluent and the composition of any one of claims 1–34, 35, 36 or 37–44.

46. A lubricant or functional fluid comprising a major amount of oil and a minor amount of the composition of any one of claims 1–34, 35, 36 or 37–44.

* * * * *

UNITED STATES PATENT AND TRADEMARK OFFICE
CERTIFICATE OF CORRECTION

PATENT NO.  : 4,507,215

DATED       : March 26, 1985

INVENTOR(S) : Schroeck, Calvin W.

It is certified that error appears in the above—identified patent and that said Letters Patent is hereby corrected as shown below:

Summary Page, Left Column:

--[73[ Assignee:- The Lubrizol Corporation, Wickliffe, Ohio--.

Summary Page, Right Column:

--Attorney, Agent or Firm:
Denis A. Polyn, Raymond F. Keller and Walter C. Danison--

Signed and Sealed this

Nineteenth Day of August 1986

[SEAL]

Attest:

DONALD J. QUIGG

Attesting Officer

Commissioner of Patents and Trademarks